United States Patent [19]

Kenyon et al.

[11] Patent Number: 4,650,882
[45] Date of Patent: Mar. 17, 1987

[54] DYES HAVING TWO 5-MEMBERED LACTONE RINGS FUSED TO A CENTRAL CYCLOHEXA-1,4-DIENE NUCLEUS

[75] Inventors: Ronald W. Kenyon, Failsworth; Derek Thorp, Heywood, both of England

[73] Assignee: Imperial Chemical Industries PLC, London, England

[21] Appl. No.: 674,317

[22] Filed: Nov. 23, 1984

[30] Foreign Application Priority Data

Dec. 16, 1983 [GB] United Kingdom ............. 8333600
Aug. 10, 1984 [GB] United Kingdom ............. 8420433

[51] Int. Cl.⁴ .................................. C07D 307/83
[52] U.S. Cl. ........................... 549/299; 549/45; 549/47; 548/431; 548/433
[58] Field of Search .................................. 549/299

[56] References Cited

U.S. PATENT DOCUMENTS 4,115,404  9/1978  Greenhalgh et al. ............. 549/299
4,122,087 10/1978  Greenhalgh et al. ............. 549/299
4,333,877  6/1982  Carey et al. ..................... 548/421

FOREIGN PATENT DOCUMENTS 2068402  1/1981  United Kingdom .
2103231  5/1982  United Kingdom .

OTHER PUBLICATIONS

Thompson et al. CA. 98:217179y.
Greenhalgh et al. CA. 95:221293m.

*Primary Examiner*—Jane T. Fan
*Attorney, Agent, or Firm*—Cushman, Darby & Cushman

[57] ABSTRACT

A novel hetero-polycyclic compound of the following formula, a method for its preparation and its use in the coloration of textile materials:

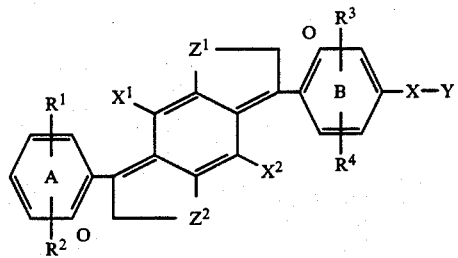

wherein, $Z^1$ & $Z^2$ are each independently —O—, —S— or —NR$^5$— in which $R^5$ is H or an optionally-substituted hydrocarbon group or an acyl group;

$X^1$ & $X^2$ are selected from H, halogen, cyano, $C_{1-4}$-alkyl, $C_{1-4}$-alkoxy, aryl, carbamoyl, sulphamoyl, carboxylic acid or carboxylic acid ester;

$R^1$ to $R^4$ are each independently selected from H, $C_{1-4}$-alkyl, $C_{1-4}$-alkoxy, $C_{1-4}$-alkenyl, halogen and the group —X—Y;

X is —O— or —S—; and
Y is a group of the formula:

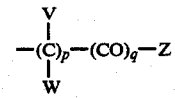

wherein:
V & W are each independently H or optionally substituted alkyl;
p is an integer from 1 to 3;
q is 0 or 1;
p+q is at least 2; and
Z is OR$^6$ or NR$^6$R$^7$ when q=1;
or Z is OR$^8$ or SR$^8$ when q=0;

wherein:
$R^6$ is selected from optionally substituted alkyl, optionally substituted alkoxyalkyl and a second group represented by Y in which $R^6$ is optionally substituted alkyl or optionally substituted alkoxyalkyl; and
$R^7$ is selected from H, and optionally substituted alkyl;
$R^8$ is selected from optionally substituted alkyl, optionally substituted alkoxyalkyl and acyl, provided that, the substituents on rings A & B are different when $Z^1$ & $Z^2$ are the same or that $Z^1$ & $Z^2$ are different when the substituents on rings A & B are the same.

9 Claims, No Drawings

DYES HAVING TWO 5-MEMBERED LACTONE RINGS FUSED TO A CENTRAL CYCLOHEXA-1,4-DIENE NUCLEUS

This specification describes an invention relating to a novel hetero-polycyclic compound, a method for its preparation and its use in the the colouration of textile materials.

According to the present invention there is provided a compound of the formula:

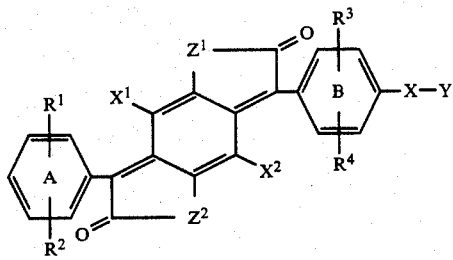

wherein, $Z^1$ & $Z^2$ are each independently —O—, —S— or —NR$^5$— in which R$^5$ is H or an optionally-substituted hydrocarbon group or an acyl group;

$X^1$ & $X^2$ are selected from H, halogen, cyano, $C_{1-4}$-alkyl, $C_{1-4}$-alkoxy, aryl, carbamoyl, sulphamoyl, carboxylic acid or carboxylic acid ester;

$R^1$ to $R^4$ are each independently selected from H, $C_{1-4}$-alkyl, $C_{1-4}$-alkoxy, $C_{1-4}$-alkenyl, halogen and the group —X—Y; X is —O— or —S—; and Y is a group of the formula:

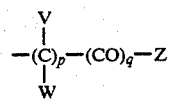

wherein:

V & W are each independently H or optionally substituted alkyl;

p is an integer from 1 to 3;

q is 0 or 1;

p+q is at least 2; and

Z is OR$^6$ or NR$^6$R$^7$ when q=1;

or Z is or OR$^8$ when q=0;

wherein:

R$^6$ is selected from optionally substituted alkyl, optionally substituted alkoxyalkyl and a second group represented by Y in which R$^6$ is optionally substituted alkyl or optionally substituted alkoxyalkyl; and R$^7$ is selected from H, and optionally substituted alkyl;

R$^8$ is selected from optionally substituted alkyl, optionally substituted alkoxyalkyl and acyl, provided that, the substituents on rings A & B are different when $Z^1$ & $Z^2$ are the same or that $Z^1$ & $Z^2$ are different when the substituents on rings A & B are the same.

The optionally substituted hydrocarbon group represented by R$^5$ is preferably $C_{1-8}$-alkyl, and more preferably $C_{1-4}$-alkyl, or monocyclic aryl, more preferably phenyl which may be substituted by groups selected from hydroxy, halogen, nitro and alkoxy. Where R$^5$ is monocyclic aryl it may also be substituted by alkyl and where R$^5$ is alkyl it may also be substituted. The acyl group represented by R$^5$ is preferably $C_{1-4}$-alkyl- or monocyclic arylcarbonyl or arylsulphonyl which may be substituted by one or more groups selected from hydroxy, halogen, nitro, $C_{1-4}$-alkyl and $C_{1-4}$-alkoxy. Examples of the optionally substituted hydrocarbon groups represented by R$^5$ are alkyl and preferably $C_{1-4}$-alkyl, such as methyl, ethyl, n-propyl and iso-propyl; substituted alkyl, preferably substituted $C_{1-4}$-alkyl, such as beta-hydroxyethyl, beta-methoxyethyl and beta-ethoxyethyl; phenyl and substituted phenyl such as tolyl, chlorophenyl, nitrophenyl and $C_{1-4}$-alkoxyphenyl. Examples of the acyl groups represented by R$^5$ are acetyl, propionyl, n-butyryl, iso-butyryl, benzoyl and m-nitrobenzoyl, p-chlorobenzoyl, p-methylbenzoyl, p-methoxybenzoyl and p-hydroxybenzoyl.

The aryl groups represented by X$^1$ and X$^2$ are preferably mono-homocyclic aryl, that is phenyl and substituted phenyl. The $C_{1-4}$-alkyl and alkoxy groups represented by X$^1$ and X$^2$ may also be subsituted and examples of suitable substituents for these and the aryl groups are hydroxy, halogen, nitro, $C_{1-4}$-alkyl and $C_{1-4}$-alkoxy. The carbamoyl and sulphamoyl groups represented by X$^1$ and X$^2$ are preferably of the formula —CONL$^1$L$^2$ or —SO$_2$NL$^1$L$^2$ wherein L$^1$ and L$^2$ are each independently hydrogan, $C_{1-4}$-alkyl or monocyclic aryl, preferably phenyl. The carboxylic acid ester groups represented by X$^1$ and X$^2$ are prefarably of the formula —COOL$^3$ wherein L$^3$ is optionally substituted alkyl, especially $C_{1-4}$-alkyl, or monocyclic aryl, especially phenyl.

Benzene rings A and B are preferably different, the difference lying in the nature and/or the number of substituents carried by each ring. The difference lies preferably in the identity of the groups R$^1$ to R$^4$ and —X—Y carried by these rings. It is preferred that R$^1$ and R$^2$ are both H, $C_{1-4}$-alkyl or $C_{1-4}$-alkoxy or that one is $C_{1-4}$-alkyl or alkoxy and the other is H and that the substituent is present in a para position. It is preferred that R$^3$ and R$^4$ are both H, $C_{1-4}$-alkyl or $C_{1-4}$-alkoxy or that one is $C_{1-4}$-alkyl or $C_{1-4}$-alkoxy and the other is H and that any substituents are in ortho positions with respect to the group —X—Y.

The optionally substituted alkyl groups represented by V and W are preferably $C_{1-4}$-alkyl and are more prefarably unsubstituted.

It is preferred that X$^1$ and X$^2$ are both hydrogen and it is also preferred that Z$^1$ and Z$^2$ are both oxygen. Under these preferred circumstances the asymmetry in the compound of Formula I is provided by a difference in substitution on benzene rings A and B. It is preferred that ring A is unsubstituted, or carries a single alkyl or alkoxy, group in the para position, and that ring B carries a single substituent represented by —X—Y.

The alkyl groups forming the whole or part of R$^6$, R$^7$ and R$^8$ are preferably $C_{1-8}$-alkyl and more preferably $C_{1-4}$-alkyl. The acyl group represented by R$^8$ is preferably optionally substituted alkyl- or aryl-carbonyl or alkyl- or aryl-sulphonyl in which the alkyl group is preferably $C_{1-4}$-alkyl and the aryl group preferably phenyl. The optional substituents for the groups represented by R$^6$, R$^7$ and R$^8$ are preferably selected from $C_{1-4}$-alkoxy, halogen, especially chlorine or bromine, cyano and hydroxy. Where R$^8$ contains an aryl group this may also be substituted by $C_{1-4}$-alkyl.

In one preferred group within Formula I, q=1, p is 1 to 3 and Z is OR$^6$ and, in another preferred group within Formula I, q=0, p=2 or 3 and Z is OR$^8$.

In a preferred group of compounds in which q=1, X is preferably —O— and p is preferably 1 or 2 and more preferably 1. It is also preferred that Z is OR$^6$ and that R$^6$ is preferably C$_{1-4}$-alkyl, C$_{1-4}$-alkoxy-C$_{1-4}$-alkyl or a second group represented by Y. When R$^6$ is a second group represented by Y it is preferred that X is —O—, V and W are H, p is 1 and Z is C$_{1-4}$-alkoxy or C$_{1-4}$alkoxy-C$_{1-4}$alkoxy. When Z is NR$^6$R$^7$ it is preferred that both R$^6$ and R$^7$ are C$_{1-4}$-alkyl.

In a preferred group of compounds in which q=0, X is preferably —O— and p is preferably 2. It is also preferred that Z is OR$^8$ and that R$^8$ is C$_{1-4}$-alkyl or C$_{1-4}$alkoxy-C$_{1-4}$-alkyl.

In a compound according to Formula I in which q=1 Y may be a group of the formula:

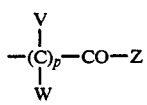

III wherein:
Z is OR$^6$ or NR$^6$R$^7$;
V & W are each independently H or optionally substituted alkyl; p is an integer from 1 to 3;
R$^6$ is selected from, alkyl, C$_{1-4}$-alkoxyalkyl, cyanoalkyl, C$_{1-4}$-alkoxy-C$_{1-4}$-alkoxyalkyl, hydroxyalkyl, haloalkyl, and a group represented by Y in which R$^6$≠Y; and
R$^7$ is selected from H, alkyl, C$_{1-4}$-alkoxyalkyl, In this group of compounds it is preferred that X is —O— and further preferred that each of V and W are H and that p is 1 or 2 and more preferably 1. It is also preferred that Z is OR$^6$ in which R$^6$ is preferably C$_{1-4}$-alkyl, C$_{1-4}$-alkoxy-C$_{1-4}$-alkyl or a group represented by Y in which X is —O—, V and W are H, p is 1 and R$^6$ is C$_{1-4}$-alkyl or C$_{1-4}$-alkoxy-C$_{1-4}$-alkyl.

The compound of Formula I, wherein Z$^1$ and Z$^2$ are both oxygen and q=1, may be prepared by reaction of a 5-hydroxy-2-oxo-3-phenyl-2,3-dihydro-benzofuran of the formula:

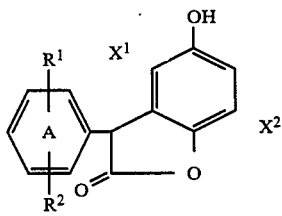

IV in which X$^1$, X$^2$, R$^1$, R$^2$ and A have the same meaning as in Formula I, with a mandelic acid, in which the 3-phenyl substituent of the dihydrobenzofuran and/or the phenyl ring of the mandelic acid carry appropriate substituents at least one of which is a group represented by —X—Y, followed by oxidation with a mild oxidising agent.

A preferred process for the preparation of a compound of Formula I wherein Z is OR$^6$ comprises the reaction of a compound of Formula IV with a mandelic acid carrying a group represented by the formula —X—T in which T has the formula:

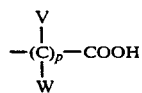

V wherein V, W and p have the same meanings as in Formula I, followed by oxidation, to form a 3,7-diphenyl-2,6-dioxo-2,6-dihydrobenzodifuran in which the 7-phenyl ring carries a substituent with a free —COOH group, i.e. a compound of the formula:

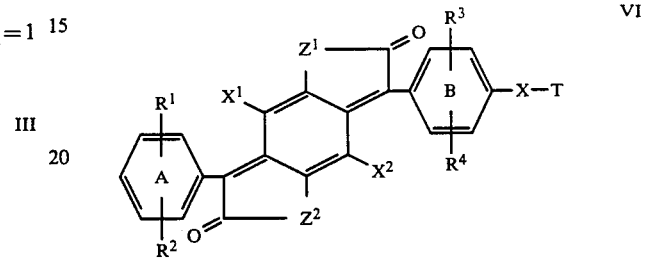

VI wherein, R$^1$ to R$^4$, A, B, Z$^1$, Z$^2$, X$^1$ X$^2$ and X are as defined in Formula I and T is a group of Formula V, and reacting this with a compound of the formula R$^6$OH, wherein V, W, p and R$^6$ have the same definitions as in Formula I, followed by oxidation. Another preferred process comprises the reaction of a compound of Formula IV with a mandelic acid carrying a group, —XH, followed by oxidation, to form a 3,7-diphenyl-2,6-dioxo-2,6-dihydro-benzodifuran in which the 7-phenyl substituent carries a group —XH, i.e. a compound of Formula VI, as hereinbefore defined except that T is H, and reacting this with a compound, U—Y wherein Y is as defined in Formula I above and U is a halogen atom, preferably chlorine or bromine. In any of the above processes the nature of the terminal —OR$^6$ group, particularly where R$^6$ is C$_{1-4}$-alkyl, may be changed by a transesterification reaction. The compound of Formula I in which R$^6$ is a second group represented by Y, can be prepared by reaction of a compound of Formula VI, in which T is of the Formula V, with a compound U—Y wherein Y has the Formula II, in which Z is OR$^6$ or NR$^6$R$^7$ provided that R$^6$≠Y.

According to a further feature of the present invention there is provided a process for the preparation of a compound according to Formula I in which Z$^1$ and Z$^2$ are oxygen and q=1 which comprises heating a mixture of a compound of the formula:

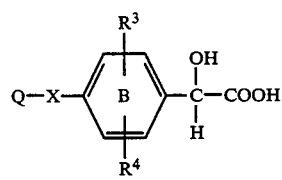

VII wherein X, R$^3$, R$^4$ and B have the same meanings as in Formula I and Q is H, Y or T with a compound of the formula:

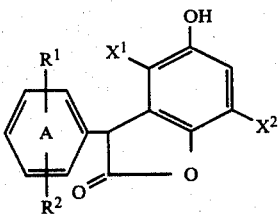

VIII wherein $X^1$, $X^2$, $R^1$, $R^2$ and A have the same meanings as in Formula I and oxidising the intermediate product to give a 3,7-diphenyl-2,6-dioxo-2,6-dihydrobenzodifuran in which the 7-phenyl ring carries a group —X—Q, i.e., a compound of Formula I except that Y=Q, followed, where Q=H, by reaction of the oxidised product with a compound of the formula U—Y or, where Q=T, by reaction of the oxidised product with a compound of the formula $R^6OH$.

The reactants of Formulae VII and VIII may be melted together but they are preferably heated in a suitable organic solvent with an acid catalyst. The melt process is preferably performed at a temperature from 190°–200° C. but the reaction in an organic solvent is preferably performed at a temperature from 50°–150° C. and more preferably from 60°–130° C. Suitable organic media are alkane carboxylic acids and their anhydrides such as acetic acid, formic acid, propionic acid and acetic anhydride; hydrocarbons and halogenated hydrocarbons such as, toluene, xylene, benzene, mesitylene, low boiling petroleum fractions, chlorobenzene, dichlorobenzene, trichlorobenzene, bromotoluene, chloronaphthalenes, dichloroethane and tetrachlorethane; nitrated hydrocarbons such as nitromethane, nitrotoluene and nitrobenzene; sulpholane; ketones such as methyl-isobutyl ketone; ethers such anisole and diphenyl ether; and esters such as methyl benzoate. Suitable acid catalysts are organic sulphonic acids such as p-toluenesulphonic acid, benzenedisulphonic acid, methanesulphonic acid; mineral acids such as sulphuric acid and hydrochloric acid; and Lewis acids such as ferric chloride and stannic chloride. Especially preferred reaction systems combine acetic acid as solvent and sulphuric acid as catalyst or chlorobenzene or toluene as solvent and p-toluenesulphonic acid as catalyst. Any convenient oxidising agent for dehydrogenating a carbon-carbon single bond may be employed for the oxidation step. Examples of suitable oxidising agents are chloranil, bromanil, benzoquinone, naphthoquinone, anthraquinone, metavanadates, persulphates, dichromates, chlorates perborates and periodates, hydrogen peroxide, vanadium pentoxide, lead and manganese dioxides and atmospheric oxygen.

The compound of Formula I wherein $Z^1$ and $Z^2$ are both oxygen and q=0 may be prepared by reaction of a compound of Formula VI in which T is H with an ester of an alcohol Y—OH and an acid, preferably an acid which is easily displaced, such as 4-methylbenzenesulphonic acid.

The compounds of Formulae IV and VIII may be prepared by the reaction of mandelic acid, or a suitable derivative thereof, with hydroquinone, using a method described in EP 33583A.

The compounds of Formula I are suitable for the coloration of synthetic textile materials, especially polyesters, giving bright orange to bluish red shades. They have high extinction coefficients in the region of 450 to 550 nm and generally build-up well on the textile material to give strong shades. They have good light fastness and very good wet and heat fastness properties. They are generally suitable for application by recognised dyeing and printing techniques for polyester textile materials and are generally superior, in high temperature dyeing processes, to the unsymmetrical dyes disclosed in UK No. 2,068,402A because they have better levelling properties. According to another feature of the present invention there is provided a process for the colouration of a synthetic textile material which comprises dyeing or printing the synthetic textile material with a dyebath liquor or a print paste containing an aqueous dispersion of a compound according to Formula I. Processes for applying the compound of Formula I to synthetic textile material are more specifically described in EP No. 33583A.

The invention is further illustrated by the following examples in which all parts and percentages are by weight unless otherwise indicated.

EXAMPLE 1

Condensation

A mixture of 11.0 g of 5-hydroxy-2-oxo-3-phenyl-2,3-dihydrobenzofuran and 11.0 g of 4-carboxymethoxymandelic acid was stirred in 75 ml 95/5 acetic/sulphuric acid for 18 hours at 110° C. 11.4 g of ammonium persulphate was added and the mixture was stirred for ½ hour at 110° C. The mixture was cooled to 25° C., poured into water and the precipitated solid filtered off, washed with water and dried.

Esterification

To 4.14 g of the 3-phenyl-7-[4-(carboxymethoxyphenyl)]2,6-dioxo-2,6-dihydrobenzo[1:2-b,4:5-b']difuran was added 250 ml of methyl cellosolve and 4 ml of sulphuric acid and the mixture stirred for ½ hour at 120° C. The mixture was cooled to 25° C., the crystalline product was filtered off, washed with methanol and dried.

The product, 3-phenyl-7-[4-(2-methoxy-ethoxycarbonylmethoxy)phenyl]-2,6-dioxo-2,6-dihydrobenzo[1:2-b,4:5-b']difuran, dissolves in chloroform to give a yellowish-red solution having an absorption maximum at 490 nm. When applied to aromatic polyester textile materials from aqueous dispersions the product gives very bright, strong scarlet shades with good build up, levelling and light fastness and excellent fastness to heat and wet treatments. When applied to polyester-cotton blends scarlet shades are produced with good all round fastness properties and good levelling.

The 4-carboxymethoxy-mandelic acid was prepared by the reaction of 18.6 g of 4-hydroxy-mandelic acid in 60 ml of water with 9.5 g of chloroacetic acid at 65° C. and at pH 12.7. The mixture was stirred for 18 hours, cooled to 25° C. and acidified by addition of hydrochloric acid. The white precipitate was filtered off, washed with acetone and dried.

EXAMPLE 2

A mixture of 1.6 g of 3-phenyl-7-(4-hydroxyphenyl)-2,6-dioxo-2,6-dihydrobenzo[1:2-b,4:5-b']difuran, 1.38 g of potassium carbonate, 1.5 g of methyl bromoacetate and 25 ml of sulpholane was stirred at 110° C. for 2 hours. The mixture was cooled to 25° C., poured into water and acidified by addition of hydrochloric acid. The precipitated solid was filtered off, washed with water and dried.

The product, 3-phenyl-7-[4-(methoxycarbonylmethoxy)phenyl]-2,6-dioxo-2,6-dihydrobenzo[1:2-b,4:5-b']difuran, dissolves in chloroform to give a yellowish-red solution having an absorption maximum at 488 nm. When applied to aromatic polyester textile materials from aqueous dispersions the product gives very bright, strong scarlet shades with good levelling and light fastness and excellent fastness to heat and wet treatments.

The 3-phenyl-7-(4-hydroxyphenyl)-2,6-dioxo-2,6-dihydrobenzo[1:2-b,4:5-b']difuran used in this example was prepared by the method described in Example 1 of UK No. 2,103,231A.

EXAMPLE 3

The procedure described in Example 2 was repeated except that in place of the 1.5 g of methyl bromoacetate there was used 1.49 g of N,N-diethyl-alpha-chloroacetamide.

The product, 3-phenyl-7-[4-(diethylaminocarbonylmethoxy)phenyl]-2,6-dioxo-2,6-dihydrobenzo[1:2-b,4:5-b']difuran, dissolves in chloroform to give a yellowish-red solution having an absorption maximum at 494 nm. When applied to aromatic polyester textile materials from an aqueous dispersion the product gives very bright, strong scarlet shades with good levelling and light fastness and excellent fastness to heat and wet treatments.

EXAMPLE 4

The esterification procedure described in Example 1 was repeated except that in place of 250 ml of methyl cellosolve there was used 250 ml of ethyl cellosolve.

The product, 3-phenyl-7-[4-(2-ethoxy-ethoxycarbonylmethoxy)phenyl]-2,6-dioxo-2,6-dihydrobenzo[1:2-b,4:5-b']difuran, dissolves in chloroform to give a yellowish-red solution having an absorption maximum at 490 nm. When applied to aromatic polyester textile materials from aqueous dispersions the product gives very bright, strong scarlet shades with good build-up, levelling and light fastness and excellent fastness to heat and wet treatments.

EXAMPLE 5

Transesterification

A mixture of 4.28 g of 3-phenyl-7-[4-(methoxycarbonylmethoxy)phenyl]-2,6-dioxo-2,6-dihydrobenzo[1:2-b,4:5-b']difuran, prepared by the method described in Example 2, 250 ml of ethyl cellosolve and 4 ml of sulphuric acid was stirred for ½ hour at 120° C. The mixture was cooled to 25° C.; the crystalline product was filtered off, washed with methanol and dried.

The product, 3-phenyl-7-[4-(2-ethoxy-ethoxycarbonylmethoxy)phenyl]-2,6-dioxo-2,6-dihydrobenzo[1:2-b,4:5-b']difuran, was identical to that obtained by the reaction described in Example 4.

EXAMPLE 6

Condensation

A mixture of 4.52 g of 5-hydroxy-2-oxo-3-phenyl-2,3-dihydrobenzofuran and 4.8 g of 4-(1-carboxy-ethoxy)-mandelic acid was stirred in 50 ml of acetic acid/sulphuric acid 95/5 for 18 hours at 110° C., following which 4.6 g ammonium persulphate was added and the mixture stirred for a further ½ hour at 110° C. The mixture was cooled to 25° C., poured into water and the precipitated solid filtered off, washed with water and driad.

Esterification

The esterification procedure described in Example 1 was repeated except that in place of 4.14 g of 3-phenyl-7-[4-(carboxymethoxy)phenyl]-2,6-dioxo-2,6-dihydrobenzo[1:2-b,4:5-b']difuran there was used 4.28 g of 3-phenyl-7-[4-(1-carboxy-ethoxy)phenyl]-2,6-dioxo-2,6-dihydro[1:2-b,4:5-b']difuran.

The product, 7-[4-(1-[2-methoxy-ethoxycarbonyl]ethoxy)phenyl]-3-phenyl-2,6-dioxo-2,6-dihydro[1:2-b,4:5-b']difuran, dissolves in chloroform to give a yellowish-red solution having an absorption maximum at 494 nm. When applied to aromatic polyester textile materials from aqueous dispersions the product gives very bright scarlet shades with good build-up, levelling and light fastness and excellent fastness to haat and wet treatments.

The 4-(1-carboxy-ethoxy)mandelic acid was prepared as described in Example 1 except that in place of 9.5 g of chloroacetic acid there was used 15.2 g of 2-bromo-propionic acid.

EXAMPLE 7

A mixture of 2.07 g 3-phenyl-7-[4-carboxymethoxy)-phenyl]-2,6-dioxo-2,6-dihydrobenzo[1:2-b,4:5-b']difuran, 1.5 g triethylamine, 3.0 g of 2-methoxyethyl chloroacetate and 40 ml of sulpholane was stirred at 110° C. for 1 hour. The mixture was cooled to 25° C., poured into water and acidified by addition of hydrochloric acid. The precipitated solid was filtered off, washed with water and dried.

The product, 3-phenyl-7-[4-(2-methoxy-ethoxycarbonylmethoxycarbonylmethoxy)phenyl]-2,6-dioxo-2,6-dihydrobenzo[1:2-b,4:5-b']difuran, dissolves in chloroform to give a yellowish-red solution having an absorption maximum at 492 nm. When applied to aromatic polyester textile materials from aqueous dispersions the product gives very bright, strong scarlet shades with good build-up, levelling and light fastness and excellent fastness to wet treatments.

EXAMPLE 8

The trans-esterification procedure described in Example 5 was repeated except that in place of the 250 ml ethyl cellosolve there was used 250 ml ethyl carbitol. The product, 3-phenyl-7-[4-(2-[2-ethoxy-ethoxy]ethoxycarbonylmethoxy)phenyl]-2,6-dioxo-2,6-dihydrobenzo[1:2-b,4:5-b']difuran, dissolves in chloroform to give a yellowish-red solution having an absorption maximum at 491 nm. When applied to aromatic polyester textile matarials from aqueous dispersions the product gives very bright, strong scarlet shades with good build-up, levelling and light fastness and excellent fastness to heat and wet treatments.

EXAMPLE 9

The procedure described in Example 2 was rapeated except that in place of the 1.5 g methyl bromoacetate there was used 2.34 g n-propyl bromobutyrate.

Transesterification

To 1.5 g of the product, 3-phenyl-7-[4-(3-[n-propoxycarbonyl]-propoxy)phenyl]-2,6-dioxo-2,6-dihydrobenzo[1:2 -b, 4:5-b']difuran was added 30 ml methyl cellosolve and 2 ml sulphuric acid and the mixture stirred for ½ hour at 120° C. The mixture was cooled to 25° C., the crystalline product was filtered off, washed with methanol and dried.

The product, 3-phenyl-7-[4-(3-[2-methoxy-ethoxycarbonyl]-propoxy)phenyl]-2,6-dioxo-2,6-dihydrobenzo[1:2-a, 4:5-b']difuran, dissolves in chloroform to give a red solution having an absorption maximum at 500 nm. When applied to aromatic polyester textile materials from aqueous dispersions the product gives very bright, strong red shades with good build-up, levelling and light fastness and excellent fastness to heat and wet treatments.

EXAMPLE 10

The esterification procedure described in Example 9 was repeated except that in place of the 30 ml methyl cellosolve there was used 30 ml ethylene glycol.

The product, 3-phenyl-7-[4-(3-[2-hydroxy-ethoxycarbonyl]-propoxy)-phenyl]- 2,6-dioxo-2,6-dihydrobenzo[1:2-a,4:5-b']difuran, dissolves in chloroform to give a red solution having an absorption maximum at 500 nm. When applied to aromatic polyester textile materials from aqueous dispersions the product gives very bright, strong red shades with good build-up, levelling and light fastness and excellant fastness to heat and wet treatments.

EXAMPLE 11

The esterification procedure described in Example 9 was repeated except that in place of the 30 ml methyl cellosolve there was used 30 ml of propane-1:2-diol.

The product, 3-phenyl-7-[4-(3-[2-hydroxy-propoxycarbonyl]-propoxy)phenyl]-2,6-dioxo-2,6-dihydrobenzo[1:2-b,4:5-b']difuran, dissolves in chloroform to give a red solution having an absorption maximum at 498 nm. When applied to aromatic polyester textile materials from aqueous dispersions the product gives very bright strong red shades with good build-up, levelling and light fastness and excellent fastness to heat and wet treatments.

EXAMPLE 12

A mixture of 7.5 g of 5-hydroxy-2-oxo-3-phenyl-2,3-dihydrobenzofuran and 6.8 g of 3-methyl-4-hydroxy mandelic acid was stirred in 50 ml 95/5 acetic/sulphuric acids for 18 hours at 110° C. 7.5 g of ammonium persulphate was added and the mixture was stirred for ½ hour at 110° C. The mixture is cooled to 25° C., poured into water and the precipitated solid filtered off, washed with watar and dried.

A mixture of 1.8 g of 3-phenyl-7-(3-methyl-4-hydroxy-phenyl)-2,6-dioxo-2,6-dihydro[1:2-b,4:5-b']difuran, 1.38 g of potassium carbonate, 1.52 g of 2-methoxy-ethyl chloroacetate and 40 ml of sulpholane was stirred at 170° C. for ½ hour. The mixture was cooled to 25° C., poured into methanol and the precipitated product filtered off, washed with water and dried.

The product 3phenyl-7[3-methyl-4-(2-methoxy-ethoxycarbonylmethoxy)phenyl]-2,6-dioxo-2,6-dihydrobenzo[1:2-b,4:5-b']difuran dissolves in chloroform to give a red solution having an absorption maximum at 497 nm. When applied to aromatic polyester materials from aqueous dispersions the product gives very bright, strong red shades with good build-up, levelling and light fastness and excellent fastness to heat and wet treatments.

EXAMPLE 13

A mixture of 1.5 g of 3-phenyl-7-(4-hydroxy-phenyl)-2,6-dioxo-2,6-dihydrobenzo[1:2-b,4:5-b']difuran, 3.6 g of 2-ethoxy-ethyl p-toluenesulphonate, 1.2 g of potassium carbonate and 25 ml of sulpholane was stirred at 140°-150° C. for 20 minutes. After cooling to 25° C., 125 ml of ethanol was added and the mixture was stirred at 25° C. for 1 hour. The product was filtered off, washed with water and then with ethanol and dried. 0.85 g of 3-phenyl-7[4-(2-ethoxy-ethoxy)-phenyl]-2,6-dioxo-2,6-dihydrobenzo[1:2-b,4:5-b']difuran was obtained which dissolves in chloform to give a red solution having an absorption maximum at 502 nm. When applied to aromatic polyester textile materials from aqueous dispersions the product gives bright red shades with good build-up, levelling and light fastness and excellent fastness to heat and wet treatments.

EXAMPLE 14

The procedure described in Example 13 was repeated except that in place of the 3.6 g of 2-ethoxy-ethyl p-toluenesulphonate there was used 3.6 g of 2-methoxy-ethyl p-toluenesulphonate. The product, 3-phenyl-7[4-(2-methoxy-ethoxy)phenyl]-2,6-dioxo-2,6-dihydrobenzo[1:2-b,4:5-b']difuran dissolves in chloroform to give a red solution having an absorption maximum at 502 nm. When applied to aromatic polyester materials it gives bright red shades with good levelling and build-up and excellent fastness to heat and wet treatments.

EXAMPLE 15

The procedure of Example 13 was repeated except that in place of the 3.6 g of 2-ethoxy-ethyl p-toluenesulphonate there was used 3.9 g of 2-(2-methoxy-ethoxy)ethyl p-toluenesulphonate. The product, 3-phenyl-7[4-(2-[2-methoxy-ethoxy]ethoxy)phenyl]-2,6-dioxo-2,6-dihydrobenzo[1:2-b,4:5-b']difuran dissolves in chloroform to give a red solution having an absorption maximum at 502 nm. It gives bright red shades on polyester with good build-up, levelling and light fastness and excellent fastness to heat and wet treatments.

EXAMPLE 16

A mixture of 2.0 g of 3-(4-methoxyphenyl)-7-[4-(ethoxycarbonylmethoxy)-phenyl]-2,6-dioxo-2,6-dihydrobenzo[1:2-b, 4:5-b']-difuran, 50 ml of methyl cellosolve and 0.5 ml of sulphuric acid was stirred for ½ hour at 120° C. The mixture was cooled to 25° C., the crystalline product was filtered off, washed with methanol and dried.

The product, 3-(4-methoxyphenyl)-7-[4-(2-methoxy-ethoxycarbonylmethoxy)-phenyl]-2,6-dioxo-2,6-dihydrobenzo[1:2-b, 4:5-b']difuran, dissolves in chloroform to give a bluish-red solution having an absorption maximum at 522 nm. When applied to aromatic polyester textile materials from aqueous dispersions the product gives bright bluish red shades with good build up, levelling and light fastness and excellent fastness to heat and wet treatments.

The 3-(4 methoxyphenyl)-7-[4-(ethoxycarbonylmethoxy)phenyl]-2,6-dioxo-2,6-dihydrobenzo[1:2-b, 4:5-b']difuran used in this example was prepared by the reaction of 7.6 g of 3-(4-methoxyphenyl)-7-(4-hydroxyphenyl)-2,6-dioxo-2,6-dihydrobenzo[1:2-b, 4:5-b']difuran in 80 ml of sulpholane and 2.8 g of potassium carbonate with 5.4 g of ethyl bromoacetate at 130° C. for 4 hours. The mixture was cooled to 25° C., poured into methanol and the precipitated solid filtered off, washed with methanol and dried.

The 3-(4-methoxyphenyl)-7-(4-hydroxyphenyl)-2,6-dioxo-2,6-dihydrobenzo[1:2-b, 4:5-b']difuran used in this example was prepared by the reaction of 40 g of 4-hydroxymandelic acid with 38 g of 5-hydroxy-2-oxo-3(4-methoxyphenyl)-2,3-dihydrobenzofuran in 200 ml 95/5 acetic/sulphuric acid for 18 hours at 110° C. 33.0 g of ammonium persulphate was added and the mixture was stirred for ½ hour at 110° C. The mixture was cooled to 25° C., poured into water and the precipitated solid filtered off, washed with water and dried.

The 5-hydroxy-2-oxo-3(4-methoxyphenyl)-2,3-dihydrobenzofuran used in this example was prepared by the reaction of 36.4 g of 4-methoxymandelic acid and 22.0 g of hydroquinone in 200 ml 95/5 acetic/sulphuric acid for 18 hours at 25° C. The mixture was poured into water, the precipitated solid filtered off, washed with water and dried.

EXAMPLE 17

A mixture of 1.9 g of 3-(4 methoxyphenyl)-7-(4-hydroxyphenyl)-2,6-dioxo-2,6-dihydrobenzo[1:2-b, 4:5-b']difuran (as described in Example 16), 2.3 g of 2-methoxyethyl-p-toluene sulphonate, 1.3 g of potassium carbonate and 30 ml of sulpholane was stirred at 130° C. for 30 minutes. After cooling to room temperature a mixture of 50 ml of methanol and 50 ml of water was added and the mixture stirred for 1 hour. The product was filtered off, washed with water and then with methanol and dried.

The product, 3-(4-methoxyphenyl)-7(4-[2-methoxyethoxy]phenyl)-2,6-dioxo-2,6-dihydrobenzo[1:2-b, 4:5-b']difuran, dissolves in chloroform to give a bluish-red solution having an absorption maximum at 530 nm. When applied to aromatic polyester textile materials from aqueous dispersions the product gives bright bluish red shades with good build up, levelling and light fastness and excellent fastness to heat and wet treatments.

EXAMPLE 18

A mixture of 2.07 g of 3-phenyl-7-[4-(carboxymethoxy)-phenyl]-2,6-dioxo-2,6-dihydrobenzo[1:2-b, 4:5-b']difuran, 2.2 g of N,N-diethyl-alpha-chloroacetamide, 1.5 g of triethylamine and 30 ml of sulpholane was stirred at 110° C. for 1 hour. Aftar cooling to room temperature methanol was added, the product was filtered off, washed with water and then with methanol and dried.

The product, 3-phenyl-7-[4-(diethylaminocarbonylmethoxy carbonylmethoxy)-phenyl]-2,6-dioxo-2,6-dihydrobenzo[1:2-b, 4:5-b']difuran, dissolves in chloroform to give a yellowish-red solution having an absorption maximum at 492 nm. When applied to aromatic polyester textile materials from an aqueous dispersion the product gives very bright, strong scarlet shades with good levelling and light fastness and excellent fastness to heat and wet treatments.

EXAMPLE 19

A mixture of 2.26 g of 5-hydroxy-2-oxo-3-phenyl-2,3-dihydrobenzofuran and 2.12 g of 4-(2-hydroxyethoxy)-mandelic acid was stirred in 20 ml 95/5 acetic/sulphuric acid for 4 hours at 110° C. 2.24 g of ammonium persulphate was added and the mixture stirred for ½ hour at 10° C. The mixture was cooled to 25° C., poured into water and the precipitated solid filtered off, washed with water and then with methanol and dried.

The product, 3-phenyl-7-[4-(2-acetoxyethoxy)-phenyl]-2,6-dihydro-2,6-dihydrobenzo[1:2-b, 4:5=b']difuran, dissolves in chloroform to give a yellowish-red solution having an absorption maximum at 496 nm. When applied to aromatic polyester textile materials from aqueous dispersions the product gives bright, strong yellowish-red shades with good levelling and light fastness and excellent fastness to heat and wet treatments.

The 4-(2-hydroxyethoxy)mandelic acid used in this example was prepared by the method described in Example 1 for the preparation of 4-carboxymethoxymandelic acid except that in place of chloroacetic acid there was used 2-bromoethanol.

EXAMPLE 20

A mixture of 1.0 g of 3-phenyl-7-(4-[2-hydroxyethoxy]phenyl)-2,6-dioxo-2,6-dihydrobenzo[1:2-b, 4:5-b']difuran, 25 ml of pyridine and 1.0 g of methoxyacetyl chloride was stirred and heated at 90°-95° C. for ½ hour. The mixture was cooled to 25° C., poured into water and the precipitated solid filtered off, washed with water and then with methanol and dried.

The product, 3-phenyl-7-(4-[2-(methoxyacetoxy)ethoxy]phenyl)-2,6-dioxo-2,6-dihydrobenzo[1:2-b, 4:5-b']difuran, dissolves in chloroform to give a red solution having an absorption maximum at 496 nm. When applied to aromatic polyester textile materials from aqueous dispersions the product gives bright red shades with good levelling and build-up and excellent fastness to heat and wet treatments.

The 3-phenyl-7-(4-[2-hydroxyethoxy]phenyl)-2,6-dioxo-2,6-dihydrobenzo[1:2-b, 4:5-b']difuran used in this Example was prepared by hydrolysis of the acetoxy derivative prepared as in Example 19 with 68% sulphuric acid at 100° C.

EXAMPLE 21

A mixture of 0.5 g of 3-phenyl-7-[3,5-dimethyl-4-(ethoxycarbonylmethoxy-phenyl]-2,6-dioxo-2,6-dihydrobenzo-[1:2-b, 4:5-b']difuran, 25 ml of methyl cellosolve and 0.1 ml sulphuric acid was stirred for 1 hour at 120° C. The mixture was cooled to 25° C., the crystalline product was filtered off, washed with methanol, water and dried.

The product, 3-phenyl-7-[3,5-dimethyl-4-(2-methoxyethoxycarbonylmethoxy)-phenyl]-2,6-dioxo-2,6-dihydrobenzo[1:2-b, 4:5-b']difuran, dissolves in chloroform to give an orange solution having an absorption maximum at 480 nm. When applied to aromatic polyester textile materials from aqueous dispersions the product gives bright orange shades with good build-up, levelling and light fastness and excellent fastness to heat and wet treatments.

The 3-phenyl-7-[3,5-dimethyl-4-(ethoxycarbonylmethoxy)phenyl]-2,6-dioxo-2,6-dihydrobenzo[1:2-b, 4:5-b']difuran used in this example was prepared by the reaction of 3.84 g of 3-phenyl-7-(3,5-dimethyl-4-hydroxyphenyl)-2,6-dioxo-2,6-dihydrobenzo[1:2-b, 4:5-b']difuran in 70 ml of sulpholane and 1.52 g of potassium carbonate with 1.84 g of ethyl bromoacetate at 160° C. for 1 hour. The mixture was cooled to 25° C., poured into methanol and the precipitated solid filtered off, washed with methanol and dried.

The 3-phenyl-7-(3,5-dimethyl-4-hydroxyphenyl)-2,6-dioxo-2,6-dihydrobenzo[1:2-b, 4:5-b']difuran used in this example was prepared by the reaction of 42 g of 3,5-dimethyl-4-hydroxymandelic acid with 22.6 g of 5-hydroxy-2-oxo-3-phenyl-2,3-dihydrobenzofuran in 200 ml 95/5 acetic/sulphuric acid for 18 hours at 110° C. 33.0 g of ammonium persulphate was added and the mixture stirred for 1 hour at 110° C. The mixture was cooled to 25° C., poured into water and the precipitated solid filtered off, washed with water and dried.

The 3,5-dimethyl-4-hydroxymandelic acid used in this example was prepared by the reaction of 65.0 g of 2,6-dimethylphenol with 62.7 g of 50% w/w glyoxylic acid solution in 180 ml water, adjusted to pH 10.5 with sodium hydroxide liquor and stirred for 18 hours at 45°–50° C. The mixture was cooled to 25° C., adjusted to pH 5.5 with hydrochloric acid and extracted with methyl-isobutyl ketone. The aqueous phase was run off, 150 g of sodium chloride added and the mixture stirred for 1 hour. The precipitated solid was filtered off and dried.

EXAMPLE 22

A mixture of 1.0 g of 3-phenyl-7-(4-hydroxyphenyl)-2,6-dioxo-2,6-dihydrobenzo[1:2-b, 4:5-b']difuran, 3.0 g of methoxyethoxyethyl-p-toluene sulphonate, 0.8 g of potassium carbonate and 15 ml of sulpholane, was stirred at 140°–150° C. for ½ hour. After cooling to 25° C., 75 ml of water was added and the product filtered off, washed with water and then with methanol and dried. The product was purified by extraction into ethyl acetate, evaporation of the solvent and washing the residue with methanol.

The product, 3-phenyl-7-(4-[methoxyethoxyethoxy]phenyl)-2,6-dioxo-2,6-dihydrobenzo[1:2-b, 4:5-b']difuran, dissolves in chloroform to give a red solution with an absorption maximum at 502 nm. When applied to polyestar textile materials from aqueous dispersions it gives bright red shades with good build up and good levelling and excellent fastness to heat and wet treatments.

EXAMPLE 23

A mixture of 1.5 g of 3-phenyl-7-(4-hydroxy-3-methylphenyl)2,6-dioxo-2,6-dihydrobenzo[1:2-b, 4:5-b']difuran, 3.2 g of 2-methoxyethyl-p-toluane sulphonate (prepared as in Example 12), 1.2 g of potassium carbonate and 20 ml of sulpholane was stirred at 140°–150° C. for ½ hour. After cooling to 25° C., 75 ml of ethanol was added and the mixture stirred at 25° C. for 1 hour.

The product, 3-phenyl-7-[4-(2-methoxyethoxy)-3-methylphenyl]-2,6-dioxo-2,6-dihydrobenzo[1:2-b, 4:5-b']difuran, was filtered off, washed with methanol and dried. It dissolves in chloroform to give a red solution having an absorption maximum at 508 nm. When applied to aromatic polyester textile materials from aqueous dispersions the product gives bright bluish-red shades with good build-up and good levelling with excellent fastness to heat and wet treatments.

EXAMPLE 24

A mixture of 2.26 g of 5-hydroxy-2-oxo-3-phenyl-2,3-dihydrobenzofuran, 2.26 g of 4-carboxymethoxymandelic acid, 1.9 g of p-toluene sulphonic acid and 25 ml of monochlorobenzene was stirred under reflux for 18 hours. 2.5 g of chloranil was added and the mixture stirred under reflux for 1 hour. The mixture was cooled to 25° C. and the product, 3-phenyl-7-[4-(carboxymethoxy)phenyl]-2,6-dioxo-2,6-dihydrobenzo[1:2-b, 4:5-b']difuran, filtered off, washed with chlorobenzane, methanol, water and finally methanol. The yield was 3.33 g.

The above product was added to 75 ml of methyl cellosolve and 3 ml of sulphuric acid and the mixture stirred at 90°–95° C. for 5 hours. The mixture was cooled to 25° C. and the crystalline product was filtered off, washed with methanol and dried. The yield was 2.57 g.

The product, 3-phenyl-7-[4-(2methoxyethoxycarbonylmethoxy)-phenyl]-2,6-dioxo-2,6-dihydrobenzo[1:2-b, 4:5-b']difuran, was identical to that obtained by the reaction described in Example 1.

In place of the 2.5 g of chloranil used in this example there can be used 4.1 g of bromanil or 1.1 g benzoquinone.

In place of the 1.9 g of p-toluene sulphonic acid used in this example there can be used 1.6 g of benzenesulphonic acid or 1.0 g of methane sulphonic acid.

EXAMPLE 25

A mixture of 1.5 g of 3-(4-methylphenyl)-7-(4-hydroxyphenyl)-2,6-dioxo-2,6-dihydrobenzo[1:2-b, 4:5-b']difuran, 3.6 g of 2-(2-methoxyethoxy)ethyl-p-toluene sulphonate, 1.2 g of potassium carbonate and 20 ml of sulpholane was stirred at 140°–150° C. for 25 minutes. After cooling to 25° C., 75 ml of 50% aqueous ethanol was added and the mixture stirred at 25° C. for ½ hour. The product was filtered off, washed with water and then with ethanol and dried.

The product, 3-(4-methylphenyl)-7-[4-(2-[2-methoxyethoxy]ethoxy)phenyl]-2,6-dioxo-2,6-dihydrobenzo[1:2-b, 4:5-b']difuran, dissolves in chloroform to give a red solution having an absorption maximum at 509 nm. When applied to aromatic polyester textile materials from aqueous dispersions it gives bright bluish-red shades with good build-up and good levelling and with excellent fastness to heat and wet treatments.

The 3-(4-methylphenyl)-7-(4-hydroxyphenyl)-2,6-dioxo-2,6dihydrobenzo[1:2-b, 4:5-b']difuran, used in this example was prepared by reaction of 13.55 g of 4-hydroxymandelic acid (of 62% strength) with 12.0 g of 5-hydroxy-2-oxo-3(4-methylphenyl)-2,3-dihydrobenzofuran in 80 ml acetic/sulphuric acid (95/5) for 18 hours at 95°–100° C. 12.0 g of ammonium persulphate was added and the mixture was stirred for 1 hour at 95°–100° C. The mixture was cooled to 25° C., added to 500 ml of water and the precipitated solid filtered off, washed with water and then methanol and dried.

The 5-hydroxy-2-oxo-3(4-methylphenyl)-2,3-dihydrobenzofuran was prepared by reaction of 16.6 g of 4-methylmandelic acid with 19.25 g of hydroquinone in 100 ml of 73% sulphuric acid at 80° C. for 2½ hours. After cooling to 25° C. the mixture was added to 500 ml of water and the product filtered off, washed acid free with water and dried.

EXAMPLE 26

In place of the 75 ml of 95/5 acetic/sulphuric acid used in Example 1 there can be used 75 ml of 95/5 propionic/sulphuric acid.

EXAMPLE 27

In place of the 75 ml of 95/5 acetic/sulphuric acid used in Example 1 there can be used a mixture of 75 ml of acetic acid and 9.5 g of p-toluene sulphonic acid.

EXAMPLE 28

In place of the 75 ml of 95/5 acetic/sulphuric acid used in Example 1 there can be used a mixture of 75 ml of acetic acid and 4.8 g of methane sulphonic acid.

We claim:
1. A compound of the formula:

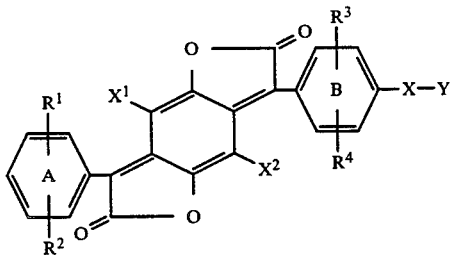

wherein
X$^1$ and X$^2$ are selected from H, halogen, cyano, C$_{1-4}$-alkyl, C$_{1-4}$-alkoxy, phenyl, CONL$^1$L$^2$, SO$_2$NL$^1$L$^2$, COOH, COOL$^3$, and substituted alkyl, alkoxy and phenyl in which the substituents are selected from hydroxy, halogen, nitro, C$_{1-4}$-alkyl and C$_{1-4}$-alkoxy;

L$^1$, L$^2$ and L$^3$ are selected from H, C$_{1-4}$-alkyl and phenyl;

R$^1$ to R$^4$ are independently selected from H, C$_{1-4}$-alkyl, C$_{1-4}$-alkoxy, C$_{1-4}$-alkenyl, halogen and the group —X—Y;

X is —O—, or —S—;
and Y is a group of the formula:

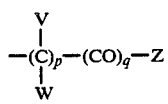

wherein,
V and W are each independently H or C$_{1-4}$-alkyl;
p is an integer from 1 to 3;
q is 0 or 1;
p+q is at least 2;
and Z is OR$^6$ or NR$^6$R$^7$ when q=1;
or Z is OR$^8$ or SR$^8$ when q=0;
wherein,
R$^7$ is selected from H, C$_{1-8}$-alkyl and C$_{1-8}$-alkyl substituted by a group selected from C$_{1-4}$-alkyl, halogen, cyano and hydroxy;

R$^8$ is selected from C$_{1-8}$-alkyl, C$_{1-8}$-alkoxyalkyl and C$_{1-4}$-alkyl-carbonyl or sulphonyl and phenylcarbonyl or sulphonyl in which the alkyl groups are unsubstituted or substituted by a group selected from C$_{1-4}$-alkoxy, halogen, cyano and hydroxyl, and the phenyl groups are unsubstituted or substituted by C$_{1-4}$-alkyl;

and R$_6$ is selected from C$_{1-8}$-alkyl, C$_{1-8}$-alkoxyalkyl, in which the alkyl and alkoxyalkyl groups are unsubstituted or substituted by a group selected from C$_{1-4}$-alkyl, halogen, cyano and hydroxy, and a group of the formula:

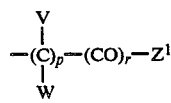

wherein

V, W and p are as hereinbefore defined;
r is 0 or 1;
and Z$^1$ is OR$^9$ or NR$^9$R$^7$ when r=1;
or Z$^1$ is OR$^8$ or SR$^8$ when r=0;
R$^7$ and R$^8$ are as hereinbefore defined;
and R$^9$ is selected from C$_{1-8}$-alkyl and C$_{1-8}$-alkoxyalkyl, in which the alkyl and alkoxyalkyl groups are unsubstituted or substituted by a group selected from C$_{1-4}$-alkyl, halogen, cyano and hydroxy provided that, the substituents on rings A and B are different when Z$^1$ and Z$^2$ are the same or that Z$^1$ and Z$^2$ are different when the substituents on rings A and B are the same.

2. A compound according to claim 1 wherein X$^1$ and X$^2$ are both H.

3. A compound according to any one of claims 1 to 2 wherein R$^1$ is H and R$^2$ is H, C$_{1-4}$-alkyl or C$_{1-4}$-alkoxy in a para position.

4. A compound according to any one of claims 1, 2 and 3 wherein R$^3$ and R$^4$ are each independently H, C$_{1-4}$-alkyl or C$_{1-4}$-alkoxy in ortho positions with respect to the group —X—Y.

5. A compound according to any one of claims 1 to 3 wherein q=0, p=2 or 3 and Z is OR$^8$.

6. A compound according to claim 5 wherein p=2 and R$^8$ is C$_{1-4}$alkyl or C$_{1-4}$alkoxy-C$_{1-4}$-alkyl.

7. A compound according to claim 1 wherein X$^1$, X$^2$ and R$^1$ to R$^4$ are H, Z$^1$, Z$^2$ and X are —O— and Y is C$_{1-4}$-alkoxyethoxycarbonylmethyl.

8. A compound according to claim 1 wherein X is —O—, q=1, p=1 to 3 and Z is OR$^6$ or NR$^6$R$^7$ in which R$^7$ is selected from H, C$_{1-4}$-alkyl, C$_{1-4}$-alkoxy-C$_{1-4}$-alkyl and cyano-C$_{1-4}$-alkyl and R$^6$ is selected from C$_{1-4}$-alkyl, C$_{1-4}$-alkoxy-C$_{1-4}$-alkyl, cyano-C$_{1-4}$-alkyl, C$_{1-4}$-alkoxy-C$_{1-4}$-alkoxy-C$_{1-4}$-alkyl, hydroxy-C$_{1-4}$-alkyl, halo-C$_{1-4}$-alkyl and a group of the formula:

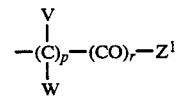

wherein
V, W, and p are as defined in claim 12;
r is 0 or 1;
and Z$^1$ is OR$^9$ or NR$^9$R$^7$ when r=1;
or Z$^1$ is OR$^8$ or SR$^8$ when r=0;
R$^7$ & R$^8$ are as defined in claim 12;
and R$^9$ is selected from C$_{1-8}$-alkyl and C$_{1-8}$-alkoxyalkyl, in which the alkyl and alkoxyalkyl groups are unsubstituted or substituted by a group selected from C$_{1-4}$-alkyl, halogen, cyano and hydroxy.

9. A compound according to claim 8 wherein p=1 and R$^6$ is selected from C$_{1-4}$-alkyl, C$_{1-4}$-alkoxy-C$_{1-4}$-alkyl and a group of the formula:

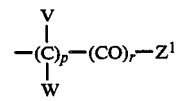

in which V and W are H, p=1, r=1 and Z$^1$ is C$_{1-4}$-alkyl or C$_{1-4}$-alkoxy-C$_{1-4}$-alkyl.

* * * * *